United States Patent
Koga et al.

(10) Patent No.: US 8,492,421 B2
(45) Date of Patent: Jul. 23, 2013

(54) AGENT FOR FUNGAL DERMATITIS

(75) Inventors: Hiroyasu Koga, Osaka (JP); Yasuko Nanjoh, Osaka (JP); Hideo Kaneda, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 490 days.

(21) Appl. No.: 12/675,441

(22) PCT Filed: Aug. 26, 2008

(86) PCT No.: PCT/JP2008/065186
§ 371 (c)(1),
(2), (4) Date: Apr. 13, 2010

(87) PCT Pub. No.: WO2009/028495
PCT Pub. Date: Mar. 5, 2009

(65) Prior Publication Data
US 2010/0249202 A1    Sep. 30, 2010

(30) Foreign Application Priority Data

Aug. 27, 2007 (JP) ................. 2007-219333
Nov. 9, 2007 (JP) ................. 2007-292284

(51) Int. Cl.
*A61K 31/415* (2006.01)
*A61K 31/385* (2006.01)
*A61K 9/00* (2006.01)

(52) U.S. Cl.
USPC ............. 514/397; 514/440; 424/400

(58) Field of Classification Search
USPC ................. 514/397, 440; 424/400
See application file for complete search history.

(56) References Cited

U.S. PATENT DOCUMENTS

| 4,942,162 A | 7/1990 | Rosenberg et al. |
| 5,391,558 A | 2/1995 | Seo et al. |
| 5,900,488 A | 5/1999 | Kodama et al. |

FOREIGN PATENT DOCUMENTS

| JP | 05-271226 A | 10/1993 |
| JP | 09-100279 A | 4/1997 |
| JP | 2000-159750 A | 6/2000 |
| JP | 2000-302737 A | 10/2000 |
| JP | 2001-518879 A | 10/2001 |
| JP | 2002-193755 A | 7/2002 |
| JP | 2005-104924 A | 4/2005 |
| JP | 2006-306734 A | 11/2006 |
| JP | 2006-335676 A | 12/2006 |
| JP | 2007-508320 A | 4/2007 |
| JP | 2007084496 A * | 4/2007 |
| WO | WO 98/43673 A1 | 10/1998 |
| WO | WO 98/52518 A1 | 11/1998 |
| WO | 2005/034891 A2 | 4/2005 |
| WO | WO 2005/032530 A1 | 4/2005 |

OTHER PUBLICATIONS

Machine Translation of JP 2007-84496 A.*
Tajima et al., *Journal of Investigative Dermatology*, 128: 345-351 (2008).
Chinese Patent Office, First Office Action in Chinese Patent Application No. 200880104530.3 (Apr. 20, 2010).
European Patent Office, Extended European Search Report in European Application No. 08792732.3 (Sep. 23, 2010).
Japanese Patent Office, International Search Report in International Patent Application No. PCT/JP2008/065186 (Sep. 30, 2008).
Japanese Patent Office, International Preliminary Report on Patentability in International Patent Application No. PCT/JP2008/065186 (Mar. 2, 2010).
Ford et al., *British Journal of Dermatology*, 107: 691-695 (1982).
Kishii et al., *Folia Pharmacologica Japonica*, 127(5): 408-414 (2006).
Makimura et al., "Present Status of Classification of *Malassezia* Species", http://www.pfdb.net/makimura/text/malassezia/malassezia.html. (1999).
Sugita, *Japanese Journal of Medical Mycology*, 46: 147-150 (2005).
Tajima et al., *Japanese Journal of Medical Mycology*, 46: 193-196 (2005).
Takahashi et al., *Basic Pharmacology & Therapeutics*, 8(2): 49(153)-66(170) (1998).
Uchida et al., *International Journal of Antimicrobial Agents*, 21(3): 234-238 (2003).
Uchida et al., *Japanese Journal of Medical Mycology*, 33: 217-220 (1992).
Wada et al., *Japanese Journal of Medical Mycology*, 39(*Suppl.*): 83 (1998).
Koga et al., *Journal of Infection and Chemotherapy*, 12(3): 163-165 (2006).
Niwano et al., *Antimicrobial Agents and Chemotherapy*, 42(4): 967-970 (Apr. 1998).
Watanabe et al., *Mycoses*, 49(5): 236-241 (2006).
Tajima, Mami, *Japanese Journal of Medical Mycology*, 46(3): 163-167 (2005).
Japanese Patent Office, Notice of Reasons for Refusal in Japanese Patent Application No. 2009-530126 (Mar. 5, 2013) English translation.

\* cited by examiner

*Primary Examiner* — Sreeni Padmanabhan
*Assistant Examiner* — Jody Karol
(74) *Attorney, Agent, or Firm* — Leydig, Voit & Mayer, Ltd.

(57) ABSTRACT

The invention relates to a therapeutic agent for fungal dermatitis, containing luliconazole or a pharmaceutically acceptable salt thereof as an active ingredient, and a composition for the treatment of fungal dermatitis, containing luliconazole or lanoconazole in a substantially dissolved state as an active ingredient.

11 Claims, 1 Drawing Sheet

AGENT FOR FUNGAL DERMATITIS

TECHNICAL FIELD

The present invention relates to a therapeutic agent for fungal dermatitis including seborrheic dermatitis, which contains luliconazole or lanoconazole, and a preparation composition thereof. Particularly, the present invention relates to a therapeutic agent for seborrheic dermatitis, which is effective for seborrheic dermatitis wherein *Malassezia restricta* and the like are pathogenic fungi, and a preparation composition thereof. The preparation composition particularly relates to a lotion.

BACKGROUND ART

Luliconazole is a general name of (−)-(E)-[(4R)-(2,4-dichlorophenyl)-1,3-dithioran-2-ylidene](1H-imidazol-1-yl)acetonitrile, and is known to be useful as an antifungal agent (see, for example, patent document 1). A derivative thereof and the like are known to have a skin wound healing-accelerating action (see, for example, patent document 2). In addition, lanoconazole (general name), which is a racemic compound different from luliconazole in the substituent on a benzene ring (2-chlorophenyl), is known for use as a hair cosmetic which protects the skin (scalp), highly retains components in the skin (scalp), and has a superior preventing or suppressing action on dandruff or itchiness (see, for example, patent document 3). Moreover, clinical trial of lanoconazole on seborrheic dermatitis has been reported, where an efficacy ratio-improving tendency is seen but a significant difference from a control group has not been found (see non-patent document 1).

National Publication of International Patent Application No. 2001-518879 states, "While its true cause is still a topic of debate, it has been suggested that seborrheic dermatitis can be caused by a fungal infection, which is why imidazole antifungals are so effective in its treatment. Ford et al. in *British Journal of Dermatology* vol. 107, 691-695 (1982) (non-patent document 2) describe ketoconazole as fungicidal against *Pityrosporum ovale* (*Pityrosporum orbiculare* or *Malassezia furfur*), an important etiologic factor in seborrheic dermatitis. U.S. Pat. No. 4,942,162 (patent document 4) discusses the use of imidazole antifungals, specifically ketoconazole and clotrimazole, for the treatment of psoriasis and seborrheic dermatitis" (see, for example, patent document 5).

As a method for improving a therapeutic effect on many kinds of fungal skin infections including seborrheic dermatitis, use of a blend of an active ingredient selected from many kinds of antifungal agents and at least one kind selected from the group consisting of vitamin A group and vitamin E group is known (see, for example, patent document 6). Examples of the antifungal agent also include lanoconazole in a general description.

On the other hand, with the recent development of molecular biological techniques, revise of taxonomy of the genus *Malassezia* has been ongoing from the late 1990s, and the relation between each species and various types of dermatitis has been reconsidered (see, for example, non-patent document 3). While the fungi of the genus *Malassezia* require lipid in a culture medium, the nutrient lipid varies depending on the species. Therefore, many kinds of species incapable of growing on conventional media have not been detected. From recent studies, it has been clarified by gene analysis that the fungi of the genus *Malassezia* include many unknown species (see, for example, non-patent documents 4 to 6), and the involvement of *Malassezia furfur* in the cause of seborrheic dermatitis has been reconsidered.

patent document 1: JP-A-9-100279
patent document 2: JP-A-5-271226
patent document 3: JP-A-2002-193755
patent document 4: U.S. Pat. No. 4,942,162
patent document 5: National Publication of International Patent Application No. 2001-518879
patent document 6: JP-A-2005-104924
non-patent document 1: Yakuri to Rinsho (Pharmacology and Clinical Therapy), vol. 8, no. 2, p. 49-65, March 1998.
non-patent document 2: Ford et al., British Journal of Dermatology, vol. 107, p. 691 to 695, 1982.
non-patent document 3: Koichi Makimura, "Current Status of *Malassezia* Genus Classification", http://www.pfdb.net/makimura/text/malassezia/malassezia.html.
non-patent document 4: Tajima et al., Molecular Analysis of *Malassezia* Species Isolated from Three Cases of Akatsuki Disease (Pomade Crust), Jpn. J. Med. Mycol. vol. 46, p. 193-196, 2005.
non-patent document 5: Reactivity of Patient Serum IgE Antibody to *Malassezia* Separated from Atopic Dermatitis Patient, Jpn. J. Med. Mycol., 39 (Suppl.): 83, 1998.
non-patent document 6: Takashi Sugita, Genotype Analysis of the rRNA Gene of *Malassezia* Colonizing the Skin Surface of Patients with Atopic Dermatitis, Jpn. J. Med. Mycol. vol. 46, p. 147-150, 2005.

DISCLOSURE OF THE INVENTION

Problems to be Solved by the Invention

The etiology of seborrheic dermatitis has not yet been clarified completely. While infection with the fungus of the genus *Malassezia* is among the recited causes, pathogenic fungal strain is not clear.

It has been found that a preparation containing ketoconazole, which is one kind of imidazole antifungal agents, as an active ingredient is effective for the treatment of seborrheic dermatitis. However, its effect in the clinical use is not necessarily sufficient. One reason therefor is an unspecified important pathogenic fungal species. Generally, antifungal activity of imidazole agents is not potent against yeasts, and the effect tends to vary depending on the strain and the like. Even when these imidazole antifungal agents are tested on certain species and strains and good biological activities are observed, these medicaments would have been less effective in many actual clinical cases where a different strain is a pathogenic fungal strain. First specifying a true or more important pathogenic fungal strain was the important problem. The fungi of the genus *Malassezia* considered to be the pathogenic fungi were not easy to cultivate. While culture of the fungi of the genus *Malassezia* requires a certain kind of lipid, culture thereof is not easy since the required lipid component varies depending on the species. It is a more difficult problem to accurately evaluate the activity of a medicament without an influence of the supplemented lipid in a medium suitable for the pathogenic fungal strain. As mentioned above, an important problem for the treatment of seborrheic dermatitis is to specify an important pathogenic fungal strain of seborrheic dermatitis and find an active ingredient and a composition formulation having a high effect on the specified species.

Application of an antifungal agent to patients with fungal dermatitis faces various problems of composition formulation. As a preparation having a high effect on tinea pedis and the like, a cream preparation and the like are available. However, a preparation composition suitable for seborrheic dermatitis has not been sufficiently established. Particularly, a preparation composition containing luliconazole or lanoconazole, which is suitable for seborrheic dermatitis, has not been established. A cream agent and the like do not show sufficient extensibility, and are not suitable for application to a wide area of the scalp where the hair is grown. In contrast, a liquid agent and the like are superior in the extensibility; however, for application to scalp and the like, a preparation free of dripping is necessary in consideration of the risk of entering the eye, reachability of the active ingredient and the like. For use on a comparatively sensitive skin such as facial surface and the like, and a rough skin suffering from inflammation, moreover, low skin irritation is obviously necessary. Furthermore, for a treatment, a superior feeling during use (good extensibility (spreadability), no trouble such as stickiness and the like) is also required.

In order to exert a sufficient biological effect using an antifungal agent containing a poorly water-soluble active ingredient, the preparation is desirably free of time-course crystallization and the like, wherein the active ingredient is preferably substantially in a dissolved state. Generally, such a liquid agent requires a large amount of an oily base, which enhances stimulation. To avoid skin irritation and the like, the preparation needs to be based on water as much as possible, and some idea different from usual is necessary to maintain the dissolved state of the active ingredient.

The aforementioned preparation free of dripping requires a certain level of viscosity. As a method of increasing the viscosity, use of cetostearyl alcohol and xanthan gum as emulsion stabilizers having a thickening effect was considered. Then, a new problem of a preparation containing luliconazole as an active ingredient was found in that addition of these emulsion stabilizers tends to cause gelling. Thus, finding of a preparation composition having appropriate viscosity and free of the gelling problem has become a new problem.

One problem of the present invention is to provide a therapeutic agent for fungal dermatitis, which shows a strong activity against a pathogenic species of fungal dermatitis, and a further problem is to provide a composition also having various properties suitable for use for the treatment of fungal dermatitis. The latter is to provide a composition for the treatment of fungal dermatitis, particularly, a composition for the treatment of seborrheic dermatitis, which has a high effect on fungal dermatitis, has appropriate extensibility that enables easy application to a wide area and appropriate viscosity free of dripping in combination, is a stable preparation free of gelling, is physicochemically stable, is free of problems of stability of the active ingredient and the like, shows sufficiently low skin irritation allowing application to the facial surface and the skin suffering from inflammation, and is superior in the feeling during use and can also be used for scalp and the like.

Means of Solving the Problems

In view of such situation and with regard to the above-mentioned problems, the present inventors started to consider the test system based on the info/wation that important pathogenic fungal strains of seborrheic dermatitis are *Malassezia restricta* and *Malassezia globosa*, and particularly, *Malassezia restricta* is deeply involved. As a result, they have succeeded in cultivating clinically separated strains of *Malassezia restricta* and *Malassezia globosa* in artificial media, and found that a dose-correlative influence can be confirmed by a treatment with a medicament. In addition, they tried to infect an experiment animal with these fungi, and could confirm development of symptoms similar to those of seborrheic dermatitis in human. They could confirm infestation and increase of *Malassezia restricta* and/or *Malassezia globosa* at the infected skin by a microscopic observation. Moreover, they could confirm that the above-mentioned symptoms can be relieved by the administration of a medicament.

As a result of detailed consideration, the present inventors have found that, when applied, a preparation containing luliconazole shows a superior effect of suppressing the growth of even intractable fungi irrespective of the difference in the fungal strain and the like, and extremely effectively decreases inflammatory conditions. In addition, they have found that a preparation containing luliconazole reduces application frequency and shortens treatment period. The present inventors have found a therapeutic agent for fungal dermatitis including seborrheic dermatitis, which contains luliconazole as an active ingredient and exhibits a high treatment effect irrespective of pathogenic fungal strain, can be provided. The effect on seborrheic dermatitis by the therapeutic agent for fungal dermatitis of the present invention could be confirmed to be superior to commercially available nizoral (active ingredient is ketoconazole) cream.

The present inventors also investigated the formulation of the composition thereof and found that a preparation free of gelling can be obtained by adding an oily base such as fatty acid esters and the like in an amount sufficient to dissolve the active ingredient so as to exert a high effect, adding an emulsion stabilizer such as cetostearyl alcohol and xanthan gum and the like to adjust viscosity, and appropriately controlling the blend thereof, that skin irritation can be reduced by appropriately combining 1,3-butyleneglycol and fatty acid esters, and that a composition having good extensibility even in the presence of hair and superior usability can be obtained by controlling the blend of the whole. Particularly, they have found that a composition superior in the applicability to the scalp with hair can be obtained by finishing in a lotion form.

They have also found that improvement of the effect for and superior applicability to seborrheic dermatitis and the like can be obtained by formulating the same composition not only in luliconazole but also other imidazole antifungal agents such as lanoconazole and the like. Such effects are attributable to the facts that the composition solves various problems in forming preparations such as skin irritation, stability, usability and the like, and the composition provides good effects also in terms of medicament retention. Of these imidazole antifungal agents, luliconazole shows most superior activity.

Accordingly, the present invention relates to

[1] a therapeutic agent for fungal dermatitis, comprising luliconazole or a pharmaceutically acceptable salt thereof as an active ingredient;

[2] the agent of the above-mentioned [1], which is a therapeutic agent for seborrheic dermatitis;

[3] the agent of the above-mentioned [1] or [2], wherein the pathogenic fungus is the fungus of the genus *Malassezia*;

[4] the agent of the above-mentioned [3], wherein the fungus of the genus *Malassezia* is *Malassezia restricta* and/or *Malassezia globosa*;

[5] a composition for the treatment of fungal dermatitis, comprising (1) luliconazole or lanoconazole, or a pharmaceutically acceptable salt thereof in a substantially dissolved state as an active ingredient, (2) an oily base, (3) 0.5 to 3% by mass of an emulsifier relative to the total amount of the composition, (4) water and (5) 0.5 to 1.5% by mass of an emulsion stabilizer relative to the total amount of the composition;

[6] the composition of the above-mentioned [5], further comprising (6) a solubilizing agent;

[7] the composition of the above-mentioned [5] or [6], which has a dosage form of a lotion;
[8] the composition of any of the above-mentioned [5] to [7], comprising, as an emulsifier, polysorbates and sorbitan monostearate at a mixing ratio (polysorbates:sorbitan monostearate) of 2:1 to 0.6:1 in mass ratio, in an amount of 0.5 to 3% by mass relative to the total amount of the composition;
[9] the composition of any of the above-mentioned [6] to [8], comprising, as a solubilizing agents, 3 to 10% by mass of 1,3-butyleneglycol relative to the total amount of the composition;
[10] the composition of any of the above-mentioned [6] to [9], comprising, as an emulsion stabilizer, 0.3 to 1.3% by mass of cetostearyl alcohol relative to the total amount of the composition and 0.15 to 0.35% by mass of xanthan gum relative to the total amount of the composition;
[11] a composition for the treatment of fungal dermatitis, comprising (1) 0.5 to 3% by mass of luliconazole or lanoconazole in a substantially dissolved state, (2a) 5 to 10% by mass of diisopropyl adipate, (2b) 2 to 8% by mass of medium-chain triglyceride, (3) 0.5 to 1.5% by mass of the total of polysorbates and sorbitan monostearate at a mixing ratio (polysorbates:sorbitan monostearate) of 2:1 to 0.6:1 in a mass ratio, (4) water, (5a) 0.3 to 1.3% by mass of cetostearyl alcohol, (5b) 0.15 to 0.3% by mass of xanthan gum, and (6) 3 to 10% by mass of 1,3-butyleneglycol;
[12] the composition of the above-mentioned [11], which has a dosage form of a lotion;
[13] the composition of any of the above-mentioned [5] to [12], wherein fungal dermatitis is seborrheic dermatitis;
[14] a method for treating fungal dermatitis, comprising administering an effective amount of the composition of the above-mentioned [5] to a target in need of a treatment of fungal dermatitis;
[15] a method for the treatment of fungal dermatitis, comprising administering an effective amount of luliconazole or a pharmaceutically acceptable salt thereof to a target in need of a treatment of fungal dermatitis;
[16] the method of the above-mentioned [15], wherein fungal dermatitis is seborrheic dermatitis;
[17] the method of the above-mentioned [16], wherein the pathogenic fungus is the fungus of the genus *Malassezia*;
[18] the method of the above-mentioned [17], wherein the fungus of the genus *Malassezia* is *Malassezia restricta* and/or *Malassezia globosa*;
[19] luliconazole or a pharmaceutically acceptable salt thereof for use as a therapeutic agent for fungal dermatitis;
[20] the compound of the above-mentioned [19] or a pharmaceutically acceptable salt thereof, wherein fungal dermatitis is seborrheic dermatitis;
[21] the compound of the above-mentioned [19] or [20] or a pharmaceutically acceptable salt thereof, wherein the pathogenic fungus is the fungus of the genus *Malassezia*;
[22] the compound of the above-mentioned [21] or a pharmaceutically acceptable salt thereof, wherein the fungus of the genus *Malassezia* is *Malassezia restricta* and/or *Malassezia globosa*, and the like.

Effect of the Invention

The therapeutic agent for fungal dermatitis of the present invention shows a high antifungal effect against fungi causing various types of dermatitis including *Malassezia restricta*, and particularly shows a high treatment effect for seborrheic dermatitis. The therapeutic agent composition for fungal dermatitis of the present invention is easy to apply because of light irritability of the skin suffering from inflammation, is easy to apply to the scalp skin with hair, has good usability, is physically and chemically stable during long-term preservation of the composition, and is superior in the retention of the active ingredient in the stratum corneum of skin when in use, where the effect is superior in both suppression of fungi growth and suppression of inflammation. Along therewith, a relative effect and the like of other medicaments can also be confirmed by the method used for the evaluation of the therapeutic agent for fungal dermatitis of the present invention.

BEST MODE FOR CARRYING OUT THE INVENTION

Figure 1:
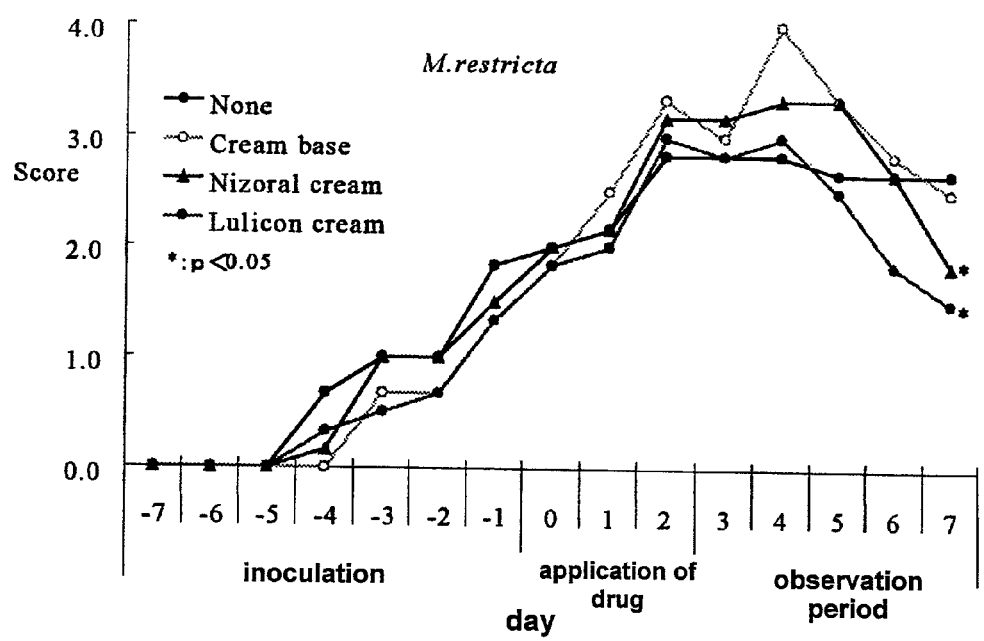
FIG. 1 is a graph showing a comparison of a skin symptom improving effect of a 1% luliconazole cream with a 2% ketoconazole cream in a seborrheic dermatitis guinea pig model (efficacy evaluation test 2).

The active ingredient to be used for the therapeutic agent for fungal dermatitis of the present invention is luliconazole. However, the active ingredient to be added is not limited to these, and may be any as long as it is effective for yeast-like fungi. In addition, the therapeutic agent for fungal dermatitis of the present invention can also contain an antifungal active ingredient besides luliconazole. Examples of such antifungal active ingredient besides luliconazole include imidazole antifungal agents such as lanoconazole, bifonazol, neticonazole, ketoconazole, clotrimazole, miconazole, oxiconazole, tioconazole, croconazole, omoconazole, sulconazole and a salt thereof and the like. In addition, antifungal agents such as benzylamine antifungal agents (butenafine and a salt thereof etc.); allylamine antifungal agents (terbinafine and a salt thereof etc.); morpholine antifungal agents (amorolfine and a salt thereof etc.); thiocarbamic acid antifungal agents (liranaftate, tolnaftate, tolciclate etc.); and antibiotics (nystatin, trichomycin, variotin, siccanin, pyrrolnitrin etc.) and the like can be exemplified.

These antifungal agents may be in the form of a salt, and a pharmaceutically acceptable salt is preferable. Examples of the pharmaceutically acceptable salt include salts with inorganic acid such as hydrochloric acid, hydrobromic acid, nitric acid, sulfuric acid, phosphoric acid and the like, salts with organic acid such as acetic acid, phthalic acid, fumaric acid, oxalic acid, tartaric acid, maleic acid, citric acid, succinic acid, methanesulfonic acid, p-toluenesulfonic acid and the like.

The "substantially in a dissolved state" includes, in addition to a maintained complete dissolution state, a state where, even when the active ingredient is crystallized under certain conditions/state of long-term, low temperature and the like, the crystals do not keep growing over time but are restorable to a dissolved state under room temperature conditions. While the amount of the antifungal active ingredient is not limited, it is about 0.5% to about 3%, preferably about 1%, in mass percentage, in consideration of solubility, skin irritation and other balances as a whole.

In the present specification, unless particularly indicated, "the amount (% by mass)" means a percentage by mass relative to the total amount of the composition.

In addition, other anti-inflammatory agents and the like can also be added as an active ingredient to suppress inflammatory conditions. Examples of such anti-inflammatory agent and antipruritic agent include sapogenins such as crotamiton, glycyrrhizinate, oleanolic acid and the like, antihistamine agents such as diphenhydramine, chlorpheniramine, chlorpheniramine maleate, dimenhydrinate, promethazine and the like, topical anesthetics such as lidocaine, dibucaine, procaine, ethyl aminobenzoate and a salt thereof and the like, allantoin, oxipolyethoxydodecan, ethyl aminobenzoate and the like.

The therapeutic agent for fungal dermatitis of the present invention can be formulated into external preparation compositions such as cream, liquid, lotion, emulsion, tincture, ointment, aqueous gel, oily gel, aerosol, powder, shampoo, soap, enamel for nail application, etc. and the like according to a conventional method by adding conventional additives and the like, which are known and used in the pharmaceutical field, as necessary. Preferred is a lotion.

The therapeutic agent for fungal dermatitis of the present invention can be transdermally administered to a treatment target, for example, mammals (e.g., mouse, rat, hamster, rabbit, cat, dog, bovine, sheep, monkey, human etc.). The therapeutic agent for fungal dermatitis of the present invention is preferably applied to an affected skin of a treatment target. Where necessary, it may be further covered with a bandage, film and the like.

The dose may be an amount permitting uniform application of the therapeutic agent for fungal dermatitis, which contains an active ingredient at a predetermined concentration, to an affected part of the skin.

The composition for the treatment of fungal dermatitis of the present invention contains, besides the above-mentioned active ingredients, an oily base, an emulsifier and an emulsion stabilizer, and may further contain, where necessary, solubilizing agent, powder component, polymer component, adhesion improver, film former, pH adjuster, antioxidant, antiseptic, preservative, agent for maintaining shape, moisturizing agent, skin protector, algefacient, flavor, colorant, chelating agent, lubricant, blood circulation promoter, astringent, tissue repair promoter, antiperspirant, plant extraction component, animal extraction component and the like, preferably solubilizing agent.

Examples of the oily base include higher alcohols such as oleyl alcohol, stearyl alcohol, cetostearyl alcohol, cetanol, benzyl alcohol and the like, fatty acid esters such as ethyl acetate, isopropyl acetate, butyl acetate, diisopropyl adipate, diethyl sebacate, isopropyl myristate, octyldodecyl oleate, octyldodecyl myristate, isostearyl myristate, lanolin and the like, medium-chain triglycerides such as beef fat, olive oil and the like, fatty acid such as squalene, squalane and the like, jojoba oil, cetaceum, white petrolatum, liquid paraffin, microcrystalline wax, terpenes such as l-menthol, d-camphor, cineol, geraniol, limonene, pulegone, thymol, aphidicolin, forskolin, phytanic acid, phytol and the like, carboxylates of terpenoids such as menthyl lactate and the like, crotamiton, esters such as diethyl ether, isopropyl ether, tetrahydrofuran, dioxane, 2-methoxyethanol, 1,2-dimethoxyethane, etc. and the like. Preferred are fatty acid esters and medium-chain triglycerides, more preferred are diisopropyl adipate, diethyl sebacate and medium-chain triglycerides, and particularly preferred are a combination of diisopropyl adipate and medium-chain triglyceride.

When the amount of the oily base is too small, the active ingredient is insufficiently dissolved therein, and when it is too high, other problems such as skin irritation and the like occur. The amount is 10 to 20%, preferably the total amount of not more than about 15%, which is an amount sufficient for dissolving the active ingredient, in mass percentage relative to the total amount of the composition. From the aspect of solubility, when the active ingredient is contained in about 1% by mass, the amount of fatty acid ester needs to be, for example, at least about 5% by mass, preferably not less than 7% by mass. Depending on the active ingredient, the amount of about 8 to 10% by mass is particularly preferable. The amount of medium-chain triglycerides in this case is preferably not less than 2% by mass, more preferably about 2 to 8% by mass, and particularly preferably about 3 to 6% by mass.

Examples of the emulsifier include polyoxyethylene hydrogenated castor oil, sorbitan monostearate, sorbitan monopalmitate, glyceryl monostearate, sorbitan monolaurate, polyoxyethylene polyoxypropylene block copolymer, polysorbates (polysorbates are fatty acid polyoxyethylene sorbitan different in the kind of fatty acid, and examples include polysorbate 60 (alias name: sorbitan polyoxyethylene monostearate (20E.O.)), polysorbate 40, Tween 40, polyoxyethylene sorbitan monopalmitate and the like), sodium lauryl sulfate, sucrose fatty acid ester, lecithin and the like. Preferred are sorbitan monostearate and polysorbates. Use of sorbitan monostearate and polysorbates in combination is particularly preferable. Of these polysorbates, polysorbate 60 is particularly preferable.

While the mixing ratio of the use of sorbitan monostearate and polysorbates in combination is not limited, from the aspect of emulsifiability, they are added such that HLB is preferably within the range of 6 to 12, more preferably 7 to 11.5, particularly preferably about 8 to 11. While the range of HLB values varies depending on the emulsifier to be used, the combination of polysorbates and sorbitan monostearate expressed in a mixing ratio in a mass ratio in consideration of the emulsion state is, for example, preferably not more than 2, more preferably not more than 1.7, of polysorbates relative to sorbitan monostearate as 1. It is particularly preferably polysorbates:sorbitan monostearate of about 1.5:1 to 1.3:1. A smaller ratio of polysorbates is preferably at least about 0.6:1.

From the aspect of skin irritation, the kind and amount of the emulsifiers are important. The amount of the emulsifiers is desirably not too high. When the amount is too small, emulsifiability becomes insufficient. The total of the two in a mass percentage is preferably about 0.5 to 3% by mass, more preferably about 0.5 to 2% by mass, further preferably about 0.5 to 1.5% by mass, particularly preferably about 0.8 to 1.5% by mass.

Examples of the solubilizing agent include water-soluble components capable of dissolving poorly water-soluble components. Examples of the component include polyvalent alcohols such as propylene glycol, 1,3-butylene glycol, glycerol and the like, low-molecular ketones such as methyl ethyl ketone, cyclohexanone and the like, macrogols and the like. Preferred is 1,3-butyleneglycol. Particularly, 1,3-butyleneglycol is preferable from the aspect of skin irritation. In comparison with propylene glycol, the skin irritation can be improved. While the amount of the solubilizing agent is not limited, it is about 3 to 10% by mass, preferably about 4 to 7% by mass, in mass percentage.

Examples of the emulsion stabilizer include higher alcohols such as cetostearyl alcohol and the like, acrylic acid polymer, carboxyvinyl polymer, polysaccharides such as xanthan gum, etc. and the like, which have a thickening effect, a film fanning effect, an adhesion improving effect, and other effects. Preferred are higher alcohols and polysaccharides, and cetostearyl alcohol and xanthan gum are particularly preferably used in combination.

The amount of the emulsion stabilizer to be added is preferably 0.5 to 1.5% by mass, more preferably 0.7 to 1.3% by mass, particularly preferably 0.75 to 1.2% by mass, relative to the total amount of the composition, in consideration of the stability test results (appearance, emulsifying particles, crystal precipitation, viscosity, yield value, component stability) and gelling of the preparation. When cetostearyl alcohol is used as an emulsion stabilizer, the amount in mass percentage is preferably 0.3 to 1.3% by mass, particularly preferably about 0.5 to 1% by mass. In this case, a combination with xanthan gum is preferable, and the amount of the xanthan gum is about 0.15 to 0.35% by mass, particularly preferably about 0.2 to 0.3% by mass.

Examples of the organic and inorganic powder components include zinc oxide, titanium oxide, magnesium stearate, talc, magnesium carbonate, magnesium oxide, silicic anhydride, silicic hydride, magnesium silicate, kaolin, AEROSIL, acid clay, mica, cornstarch, aluminum metasilicate and the like.

Examples of the polymer component include acrylic acid polymer, carboxyvinyl polymer, polysaccharides such as xanthan gum and the like, polypeptides and the like.

Examples of the adhesion improver include higher alcohols such as cetostearyl alcohol and the like, acrylic acid polymer, carboxyvinyl polymer, polysaccharides such as xanthan gum and the like, polypeptides and the like.

Examples of the film forming agent include higher alcohols such as cetostearyl alcohol and the like, acrylic acid polymer, carboxyvinyl polymer, polysaccharides such as xanthan gum and the like, polypeptides, collodion, polyvinylpyrrolidone, polyvinyl alcohol, celluloses such as nitrocellulose, etc. and the like.

Examples of the pH adjuster include organic acids such as citric acid, lactic acid, tartaric acid, stearic acid, palmitic acid, oleic acid and the like, organic acid salts such as sodium pyrophosphate and the like, inorganic bases such as sodium hydroxide and the like, organic amines such as diisopropanolamine, triethanolamine, etc. and the like.

Examples of the antioxidant include dibutylhydroxytoluene (BHT), butylhydroxyanisole (BHA), α-tocopherol, erythorbic acid, sodium pyrosulfite, sodium ascorbate and the like. Examples of the stabilizer include EDTA-2Na and the like.

Examples of the antiseptic or preservative include parabens such as methylparaben and the like, benzyl alcohol, sodium dehydroacetate, sorbic acid and the like. Examples of the agent for maintaining shape include plant-derived dextrin saccharose ester and the like. Examples of the moisturizing agent include saccharides such as sodium hyaluronate, sodium chondroitin sulfate, glycosyl trehalose, xylitol, sorbitol and the like, proteins and amino acids such as collagen, arginine, hydrolyzed silk, Sericin and the like, sodium lactate, the below-mentioned plant extraction component and the like. Examples of the skin protector include vitamin derivatives such as sodium riboflavin phosphate, magnesium ascorbyl phosphate, cyanocobalamin and the like, polyphenols such as glucosyl rutin and the like, hydroxyproline or a derivative thereof such as hydroxyproline, dipalmitoyl hydroxyproline and the like, ceramide, aminocaproic acid, siloxane derivatives such as stearoxy methylpolysiloxane, trimethylsiloxysilicate and the like, glycolipids such as cerebrosides, etc. and the like.

Examples of the algefacient include mint (1-menthol), camphor, ethanol, eucalyptus oil and the like. The colorant is not particularly limited and, for example, Red No. 202, iron oxide and the like can be mentioned. Examples of the chelating agent include EDTA-2Na (edetate), tetrasodium etidronate, pentasodium triphosphate, pentasodium pentetate and the like. Examples of the lubricant include silica, calcium stearate, magnesium stearate and the like.

Stratum corneum softening agents such as urea, organic acid esters (diethyl phthalate etc.), organic acids (lactic acid etc.), fats and oils (cetaceum, cholesterol etc.) and the like can also be added. Examples of the blood circulation promoter include benzyl nicotine, heparin analogous substance, chili pepper and the like. Examples of the astringent include aluminum chloride, aldioxa and the like. Examples of the tissue repair promoter include aluminum chlorohydroxy allantoinate, lysozyme chloride and the like. Examples of the antiperspirant include inorganic salt and organic salt or complex and a mixture thereof and the like of aluminum, zirconium or zinc such as aluminum salt, zirconium salt and the like (e.g., aluminum halide, hydroxyaluminum halide, zirconium oxyhalide, hydroxyzirconium halide, and a mixture thereof), citric acid, lactic acid, kojic acid, menthol and the like.

Examples of the plant extraction component include aloe extract, *Scutellaria baicalensis* root extract, mulberry extract, *Prunus persica* leaf extract, *Gardenia florida* leaf extract, *Eleutherococcus* extract, *Phellodendron* bark extract, *Hypericum perforatum* extract, rice polishing extract, green tea extract, *Glycyrrhiza* extract, algae extract, clove extract, Japanese angelica root extract, chili pepper extract, rosemary leaf oil and the like.

Examples of the animal extract component etc. include plant worm extract, royal jelly extract and the like.

As these pharmaceutically acceptable additives for pharmaceutical products or cosmetics etc., those generally used for preparations can be used.

Nonlimitatively, a more specific lotion as a preferable embodiment of the composition for the treatment of fungal dermatitis of the present invention uniformly contains (1) 0.5 to 3% by mass of luliconazole in a substantially dissolved state, (2a) 5 to 10% by mass of diisopropyl adipate, (2b) 2 to 8% by mass of medium-chain triglyceride, (3) 0.5 to 3% by mass of the total of polysorbates and sorbitan monostearate at a mixing ratio (polysorbates:sorbitan monostearate) of 2:1 to 0.6:1 in a mass ratio, (4) water, (5a) 0.3 to 1.5% by mass of cetostearyl alcohol, (5b) 0.15 to 0.35% by mass of xanthan gum, and (6) 3 to 10% by mass of 1,3-butyleneglycol.

The lotion can be obtained by a production method generally used for the production of pharmaceutical preparation and the like, and the dissolution step, mixing step and emulsifying step thereof can be performed in a vacuum emulsifying machine conventionally used for formulation of pharmaceutical preparations and using an anchor mixer or a homo mixer under reduced pressure (about 40 to 60 cmHg).

When the composition for the treatment of fungal dermatitis of the present invention is used for the skin with hair, for example, scalp, it is required to have viscosity suitable for good extensibility free of dripping.

The prepared lotion has viscosity of not more than 4,000 mPa·s, preferably not more than 2,000 mPa·s, at about 20° C. as measured by a rotary viscometer, where the latter particularly shows the property suitable for application to a wide area of the scalp. The emulsified state can be preserved at 25° C. for at least one year without substantial change and, even when some precipitate is produced, the original emulsified state can be easily restored by gentle shaking (several times of shaking with hand).

The pathogenic fungus of fungal dermatitis to be the application target for the therapeutic agent for fungal dermatitis of the present invention is not particularly limited as long as it belongs to a general fungi definition. So-called yeast-like fungi are important, and the *Malassezia* genus is important. More specifically, for example, *Malassezia restricta, Malassezia globosa* and *Malassezia slooffiae* and the like can be mentioned. Particularly important are *Malassezia restricta* and *Malassezia globosa*. Fungal dermatitis includes seborrheic dermatitis. Examples of other embodiments of fungal dermatitis include those mainly caused by bacteria such as *Propionibacterium acnes* and the like (e.g., acne) where *Malassezia restricta* and the like simultaneously exist, and the like.

Fungal dermatitis to be the application target for the therapeutic agent for fungal dermatitis of the present invention is not particularly limited as long as it is the skin in an inflammatory state caused by fungi, and may be human skin or skin of other animal such as mammal and the like. For example, it is effective for the treatment of a disease called malasseziosis of dogs and cats. Those called atopic dermatitis also include those caused by *Malassezia* and the therapeutic agent for fungal dermatitis of the present invention can be applied. Preferable target includes dermatitis called seborrheic dermatitis, wherein the fatty content of the skin surface is comparatively high, and dermatitis where the fungi of the genus *Malassezia* prefer to live. In bacterial dermatitis, it can also be used as an aid to the site where fungi are infected in combination. Even in such cases, it is also possible to add an antibacterial agent active ingredient to an agent for fungal dermatitis in advance.

In an in vitro (in vitro) effect test involving the fungi of the genus *Malassezia*, culture conditions including lipid is preferably used. However, a simple increase of lipid alone sometimes fails to measure the effect of a medicament. While a medium for test is not particularly limited, for example, it is preferably a modified Leeming (Leeming and Notman) medium. A more stable evaluation can be performed by adjusting the kind and amount of the lipid to be added depending on the combination of the test active ingredient and the fungi of the genus *Malassezia* and the like.

In a model test using an animal, the animal is not particularly limited. However, an animal having a skin similar to the human skin in lipid secretion and the like is preferable, and an animal suitable for efficacy evaluation is advantageous. For example, guinea pig is preferably used. Where necessary, fatty content and sugar content can be given in larger amounts, and sebum cutaneum secretion can also be promoted by administration of zinc sulfate and the like.

EXAMPLES

While specific Composition Examples of the agent for fungal dermatitis of the present invention, physicochemical property evaluation methods thereof and biological effect test methods thereof are disclosed in the following, the present invention is not limited thereto.

Composition Production Examples

Example 1

| component | (wt %) |
|---|---|
| luliconazole | 1.00 |
| cetostearyl alcohol | 1.00 |
| diisopropyl adipate | 7.00 |
| medium-chain triglyceride | 6.00 |
| polysorbate 60 | 1.50 |
| sorbitan monostearate | 0.75 |
| benzyl alcohol | 1.00 |
| 1,3-butyleneglycol | 5.00 |
| methyl p-hydroxybenzoate | 0.14 |

-continued

| component | (wt %) |
|---|---|
| dibutylhydroxytoluene | 0.02 |
| xanthan gum | 0.20 |
| purified water | 76.39 |
| total | 100.00 |

The above components were mixed to give a lotion preparation.

Example 2

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 0.70 |
| sorbitan monostearate | 1.18 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 76.76 |
| total | 100.00 |

The above components were mixed to give a lotion preparation.

Example 3

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 0.55 |
| sorbitan monostearate | 0.40 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 77.69 |
| total | 100.00 |

The above components were mixed to give a lotion preparation.

Example 4

| component | (wt %) |
|---|---|
| luliconazole | 1.00 |
| cetostearyl alcohol | 0.50 |
| diisopropyl adipate | 9.00 |
| medium-chain triglyceride | 4.00 |
| polysorbate 60 | 0.55 |

-continued

| component | (wt %) |
|---|---|
| sorbitan monostearate | 0.40 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.30 |
| purified water | 78.09 |
| total | 100.00 |

The above components were mixed to give a lotion preparation.

Example 5

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 1.10 |
| sorbitan monostearate | 0.75 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.30 |
| purified water | 76.69 |
| total | 100.00 |

The above components were mixed to give a lotion preparation.

Example 6

| component | (wt %) |
|---|---|
| luliconazole | 1.00 |
| cetostearyl alcohol | 1.00 |
| diisopropyl adipate | 7.00 |
| medium-chain triglyceride | 4.00 |
| polysorbate 60 | 0.85 |
| sorbitan monostearate | 0.60 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 79.19 |
| total | 100.00 |

The above components were mixed to give a lotion preparation.

Example 7

| component | (wt %) |
|---|---|
| luliconazole | 1.00 |
| cetostearyl alcohol | 0.50 |

-continued

| component | (wt %) |
|---|---|
| diisopropyl adipate | 9.00 |
| medium-chain triglyceride | 4.00 |
| polysorbate 60 | 0.55 |
| sorbitan monostearate | 0.40 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.25 |
| purified water | 78.14 |
| total | 100.00 |

The above components were mixed to give a lotion preparation.

Example 8

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 1.10 |
| sorbitan monostearate | 0.75 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 76.79 |
| total | 100.00 |

The above components were mixed to give a lotion preparation.

Example 9

| component | (wt %) |
|---|---|
| luliconazole | 1.00 |
| cetostearyl alcohol | 1.00 |
| diisopropyl adipate | 8.00 |
| medium-chain triglyceride | 4.00 |
| polysorbate 60 | 0.60 |
| sorbitan monostearate | 0.50 |
| benzyl alcohol | 1.00 |
| 1,3-butyleneglycol | 7.00 |
| methyl p-hydroxybenzoate | 0.14 |
| dibutylhydroxytoluene | 0.02 |
| xanthan gum | 0.30 |
| purified water | 76.44 |
| total | 100.00 |

The above components were mixed to give a lotion preparation.

Comparative Example 1

| component | (wt %) |
|---|---|
| luliconazole | 1.00 |
| cetostearyl alcohol | 1.00 |
| diethyl sebacate | 9.00 |
| medium-chain triglyceride | 4.00 |
| polysorbate 60 | 3.00 |
| sorbitan monostearate | 0.75 |
| benzyl alcohol | 1.00 |
| propylene glycol | 5.00 |
| methyl p-hydroxybenzoate | 0.14 |
| dibutylhydroxytoluene | 0.02 |
| xanthan gum | 0.20 |
| purified water | 74.89 |
| total | 100.00 |

The above components were mixed to give a lotion preparation.

Comparative Example 2

| component | (wt %) |
|---|---|
| luliconazole | 1.00 |
| cetostearyl alcohol | 1.00 |
| diethyl sebacate | 3.00 |
| medium-chain triglyceride | 4.00 |
| polysorbate 60 | 3.00 |
| sorbitan monostearate | 0.75 |
| benzyl alcohol | 1.00 |
| propylene glycol | 5.00 |
| methyl p-hydroxybenzoate | 0.14 |
| dibutylhydroxytoluene | 0.02 |
| xanthan gum | 0.20 |
| purified water | 80.89 |
| total | 100.00 |

The above components were mixed to give a lotion preparation.

Comparative Example 3

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 3.00 |
| sorbitan monostearate | 0.75 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 74.89 |
| total | 100.00 |

The above components were mixed to give a lotion preparation.

Comparative Example 4

| component | (wt %) |
|---|---|
| luliconazole | 1.00 |
| cetostearyl alcohol | 1.00 |
| diisopropyl adipate | 5.00 |
| medium-chain triglyceride | 8.00 |
| polysorbate 60 | 3.00 |
| sorbitan monostearate | 0.75 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 74.89 |
| total | 100.00 |

The above components were mixed to give a lotion preparation.

Comparative Example 5

| component | (wt %) |
|---|---|
| luliconazole | 1.00 |
| cetostearyl alcohol | 1.00 |
| diisopropyl adipate | 9.00 |
| medium-chain triglyceride | 4.00 |
| polysorbate 60 | 2.60 |
| sorbitan monostearate | 1.15 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 74.89 |
| total | 100.00 |

The above components were mixed to give a lotion preparation.

Comparative Example 6

| component | (wt %) |
|---|---|
| luliconazole | 1.00 |
| cetostearyl alcohol | 1.50 |
| diisopropyl adipate | 9.00 |
| medium-chain triglyceride | 4.00 |
| polysorbate 60 | 1.10 |
| sorbitan monostearate | 0.75 |
| benzyl alcohol | 1.00 |
| 1,3-butyleneglycol | 5.00 |
| methyl p-hydroxybenzoate | 0.14 |
| dibutylhydroxytoluene | 0.02 |
| xanthan gum | 0.20 |
| purified water | 76.29 |
| total | 100.00 |

The above components were mixed to give a lotion preparation.

Stability (Emulsifiability, Physical Performance, Component) Evaluation Test

A standing stability test was performed under various storage conditions. A cycle test wherein storage and temperature change were repeated under different temperature conditions of from −20° C. to 60° C. was performed.

Results (Visual)

TABLE 1

|  | crystallization | viscosity change |
|---|---|---|
| Example 1 | − | − |
| Example 2 | − | − |
| Example 3 | − | − |
| Example 4 | − | − |
| Example 5 | − | − |
| Example 6 | − | − |
| Example 7 | − | − |
| Example 8 | − | − |
| Example 9 | − | − |
| Comparative Example 1 | − | − |
| Comparative Example 2 | ++ | − |
| Comparative Example 3 | − | − |
| Comparative Example 4 | + | − |
| Comparative Example 5 | − | − |
| Comparative Example 6 | − | gelling |

Efficacy Evaluation Test

Efficacy evaluation test 1. Measurement of minimum inhibitory concentration by agar dilution method Using a modified Leeming (Leeming and Notman) agar medium (m-LNA, without addition of milk), the minimum inhibitory concentration (MIC) was measured by an agar dilution method. Reference publication regarding medium: Takamasa Kaneko et al., Vital growth factor *Malassezia* species on modified CHROM agar *Candida*, Medical Mycol. December 2005 43, p. 699-704.

(1) Medicament Used

As 1% luliconazole cream and 1% ketoconazole cream, commercially available preparations were purchased and used.

(2) Strain Used

As *Malassezia restricta* (*Malassezia (M.) restricta*), 10 strains (R-1 to R-10) of clinical isolates isolated and identified by Tokyo Medical University Department of Dermatology and Teikyo University Institute of Medical Mycology were used.

(3) Method

An agar dilution method. The number of days of culture for evaluation was 5 or 6 days.

(4) Results

The preparation containing luliconazole showed high activity in all strains. MIC was 0.004 to 0.016 μg/mL ($MIC_{90}$ 0.008 μg/mL), which was about 2-fold activity of that of the ketoconazole cream ($MIC_{90}$ 0.016 μg/mL).

Efficacy Evaluation Test 2. Treatment Effect on Guinea Pig Seborrheic Dermatitis Model A guinea pig seborrheic dermatitis model was prepared using *Malassezia restricta* (*Malassezia (M.) restricta*) as a pathogenic fungus, and a skin symptom improving effect and a mycological treatment effect of 1% luliconazole cream were evaluated. As a comparative drug, 2% ketoconazole cream was used.

Material and Method (1) Medicament Used

Luliconazole was prepared by the Applicant, and as 2% ketoconazole, a commercially available preparation was purchased and used.

(2) Strain Used

As *Malassezia restricta*, a clinical isolate (R-4) isolated and identified by Teikyo University Institute of Medical Mycology was used. 2.5 mL of a modified Leeming (Leeming and Notman) liquid medium (m-LN. containing olive oil) was added per 1 g wet weight of the precultured strain for suspending therein to give an inoculum.

(3) Animal Used

Male Hartley guinea pig (6-week-old at the time of inoculation) was used.

(4) Method

The hair on the back of the animal was shaved, and two inoculation sites (diameter 2 cm) were placed on either side of the back skin symmetrically. The inoculum (0.1 mL) was applied to the each site for 7 consecutive days. The medicament was applied from the next day of the completion of the inoculation at 0.1 mL/inoculation site/day for 3 days and, 5 days after the completion of the application, the animal was sacrificed and the skin was collected. The skin symptoms were observed through the experiment from the inoculation starting day to the day of sacrifice and recorded by using the score. The collected skin was prepared into paraffin-embedded slice according to a conventional method, and stained by PAS (periodic acid-Schiff staining) to identify fungus and observed under an optical microscope. The skin section was successively observed from one end to the other end and the fungal content was evaluated by the criteria shown in the Table. The detection frequency of fungus in each section was determined.

Figure 2:
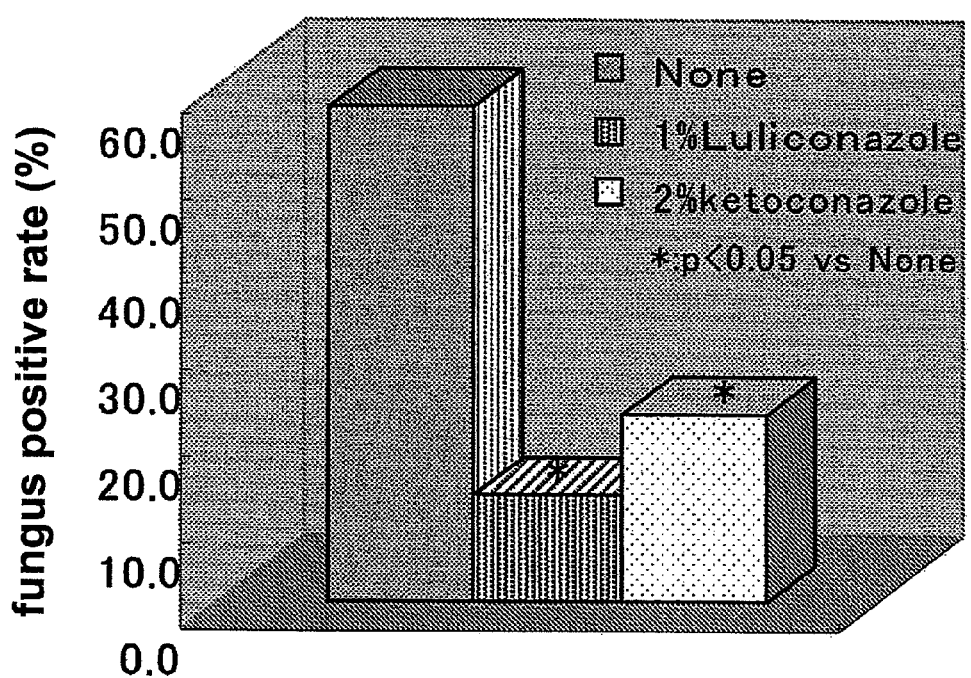
FIG. 2 is a graph showing a mycological treatment effect of a 1% luliconazole cream in a seborrheic dermatitis guinea pig model (efficacy evaluation test 2).

The observation results of the skin symptoms and histopathological fungi are shown in FIG. 1 and FIG. 2.

score symptoms 0 normal (topical lesion is not observed)

1 a small number of papular erythema which is islanded in the infected loci.

2 papular erythema is remarkable, partially swelling and some scales in spots.

3 swelling is seen in the entirety of the infected topical site, and spreads to the peripheral skin; intensed scales; sometimes solidified with invasive fluid and attached to hair.

4 swelling is remarkable, sometimes accompanying scab formation; scales are remarkable and attached to hair.

Results

Luliconazole improved skin symptom and showed mycological cure, which were superior by comparison with control medicament.

Drug Retention (Test of Drug Retention in Guinea Pig Stratum Corneum)

Experiment Method

The both hindpaw soles of guinea pig were cleaned, and a medicament was applied to the entire surface of the soles. The next day of the final application, the hindpaw soles were wiped, and the sole stratum corneum was collected by detaching. The stratum corneum was dried, and the drug was extracted and quantified by HPLC.

Results

Examples 1 to 9 showed drug retention equivalent to that of luliconazole cream.

Skin Primary Irritation Test

Lint applied with a medicament was placed on the normal and abraded back skin of Japanese white rabbit, and occlusively dressed for 24 hr (closed patch). After the treatment, observation (erythema, edema) was performed 1, 24, 48 and 72 hours later.

rank symptoms
0 not irritability.
1 mild irritation.
2 mild to moderate mild irritation.
3 moderate irritation.
4 moderate to intensive irritation.
5 intensive irritation.

Results

| | |
|---|---|
| Example 1 | 2 |
| Example 2 | 2 |
| Example 3 | 1 |
| Example 4 | 1 |
| Example 5 | 2 |
| Example 6 | 1 |
| Example 7 | 1 |
| Example 8 | 2 |
| Example 9 | 1 |
| Comparative Example 1 | 3 |
| Comparative Example 2 | 3 |
| Comparative Example 3 | 3 |
| Comparative Example 4 | 3 |
| Comparative Example 5 | 3 |
| Comparative Example 6 | 2 |

INDUSTRIAL APPLICABILITY

The agent for fungal dermatitis of the present invention shows a high effect against fungi causing various types of dermatitis including *Malassezia restricta*. Particularly, a therapeutic agent for fungal dermatitis containing luliconazole as an active ingredient shows a high treatment effect for seborrheic dermatitis. The therapeutic composition for fungal dermatitis of the present invention is easy to apply because of light irritability of the skin suffering from inflammation, is easy to apply to the scalp skin with hair, has good usability, is physically and chemically stable during long-term preservation of the composition, and is superior in the retention of the active ingredient in the stratum corneum when in use, where the effect is superior in both suppression of fungi growth and suppression of inflammation.

This application is based on Japanese patent application Nos. 2007-219333 and 2007-292284, the contents of which are all encompassed in the present specification.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A composition comprising (1) luliconazole or lanoconazole, or a pharmaceutically acceptable salt thereof in a substantially dissolved state as an active ingredient, (2) an oily base, (3) 0.5 to 3% by mass of an emulsifier relative to the total amount of the composition, (4) water and (5) 0.5 to 1.5% by mass of an emulsion stabilizer relative to the total amount of the composition, wherein the emulsifier comprises polysorbates and sorbitan monostearate at a polysorbates:sorbitan monostearate mixing ratio of 1.42:1 to 1.2:1 in mass ratio.

2. The composition according to claim 1, further comprising (6) a solubilizing agent.

3. The composition according to claim 1, which has a dosage form of a lotion.

4. The composition according to claim 2, comprising, as a solubilizing agents, 3 to 10% by mass of 1,3-butyleneglycol relative to the total amount of the composition.

5. The composition according to claim 1, comprising, as an emulsion stabilizer, 0.3 to 1.3% by mass of cetostearyl alcohol relative to the total amount of the composition and 0.15 to 0.35% by mass of xanthan gum relative to the total amount of the composition.

6. The composition according to claim 1, comprising (1) 0.5 to 3% by mass of luliconazole or lanoconazole in a substantially dissolved state, (2a) 5 to 10% by mass of diisopropyl adipate, (2b) 2 to 8% by mass of medium-chain triglyceride, (3) 0.5 to 1.5% by mass of the total of polysorbates and sorbitan monostearate at a polysorbates:sorbitan monostearate mixing ratio of 1.42:1 to 1.2:1 in a mass ratio, (4) water, (5a) 0.3 to 1.3% by mass of cetostearyl alcohol, (5b) 0.15 to 0.3% by mass of xanthan gum, and (6) 3 to 10% by mass of 1,3-butyleneglycol.

7. The composition according to claim 6, which has a dosage form of a lotion.

8. A method for treating fungal dermatitis, comprising administering an effective amount of the composition according to claim 1 to a target in need of a treatment of fungal dermatitis.

9. The method according to claim 8, wherein fungal dermatitis is seborrheic dermatitis.

10. A method for treating fungal dermatitis, comprising administering an effective amount of the composition according to claim 6 to a target in need of a treatment of fungal dermatitis.

11. The method according to claim 10, wherein fungal dermatitis is seborrheic dermatitis.

* * * * *

UNITED STATES PATENT AND TRADEMARK OFFICE
CERTIFICATE OF CORRECTION

PATENT NO. : 8,492,421 B2  
APPLICATION NO. : 12/675441  
DATED : July 23, 2013  
INVENTOR(S) : Koga et al.

Page 1 of 1

It is certified that error appears in the above-identified patent and that said Letters Patent is hereby corrected as shown below:

In the Claims:

Claim 4 at column 20, line 20, "agents" should read "agent"

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,492,421 B2  
APPLICATION NO. : 12/675441  
DATED : July 23, 2013  
INVENTOR(S) : Koga et al.

Page 1 of 1

It is certified that error appears in the above-identified patent and that said Letters Patent is hereby corrected as shown below:

*On the Title page*

References Cited, Foreign Patent Documents (right column, line 2):

"2007084496" should be "2007-084496"

*In the Specification*

Column 1, line 19:

"dithioran" should be "dithiolan"

Column 3, line 59:

"infor/wation" should be "information"

Signed and Sealed this  
Twenty-second Day of July, 2014

Michelle K. Lee  
*Deputy Director of the United States Patent and Trademark Office*